(12) United States Patent
Kingsford (10) Patent No.: US 8,439,861 B2
(45) Date of Patent: May 14, 2013

(54) SKIN PENETRATING TOUCH FASTENERS

(75) Inventor: Howard A. Kingsford, Amherst, NH (US)

(73) Assignee: Velcro Industries B.V., Willemstad, Curacao (NL)

( * ) Notice: Subject to any disclaimer, the term of this patent is extended or adjusted under 35 U.S.C. 154(b) by 1298 days.

(21) Appl. No.: 11/739,244

(22) Filed: Apr. 24, 2007

(65) Prior Publication Data

US 2008/0269670 A1    Oct. 30, 2008

(51) Int. Cl.
*A61B 17/20* (2006.01)
*A61M 37/00* (2006.01)

(52) U.S. Cl.
USPC .......................................................... 604/46

(58) Field of Classification Search .................... 604/46, 604/48, 173
See application file for complete search history.

(56) References Cited

U.S. PATENT DOCUMENTS

| | | |
|---|---|---|
| 3,964,482 A | 6/1976 | Gerstel et al. |
| 4,775,310 A | 10/1988 | Fischer |
| 5,250,023 A | 10/1993 | Lee et al. |
| 5,286,431 A | 2/1994 | Banfield et al. |
| 5,681,580 A | 10/1997 | Jang et al. |
| 5,766,385 A | 6/1998 | Pollard et al. |
| 5,819,391 A | 10/1998 | Matsushima et al. |
| 6,018,680 A | 1/2000 | Flower |
| 6,132,755 A | 10/2000 | Eicher et al. |
| 6,230,051 B1 | 5/2001 | Cormier et al. |
| 6,256,533 B1 | 7/2001 | Yuzhakov et al. |
| 6,379,324 B1 | 4/2002 | Gartstein et al. |
| 6,454,755 B1 | 9/2002 | Godshall |
| 6,463,635 B2 | 10/2002 | Murasaki |
| 6,532,386 B2 | 3/2003 | Sun et al. |
| 6,591,133 B1 | 7/2003 | Joshi |
| 6,656,147 B1 | 12/2003 | Gertsek et al. |
| 7,108,814 B2 | 9/2006 | Herrero et al. |
| 2002/0042589 A1 | 4/2002 | Marsoner |
| 2003/0135161 A1 | 7/2003 | Fleming et al. |
| 2005/0010161 A1* | 1/2005 | Sun et al. .......................... 604/20 |
| 2005/0118388 A1* | 6/2005 | Kingsford ........................ 428/99 |
| 2005/0228340 A1* | 10/2005 | Cleary et al. .................... 604/46 |

FOREIGN PATENT DOCUMENTS

| | | |
|---|---|---|
| WO | WO 99/29364 | 6/1999 |
| WO | WO 2005/110525 | 11/2005 |

OTHER PUBLICATIONS

Specification and Figures for U.S. Appl. No. 09/440,384, "Skin Attachment Member", Howard A. Kingsford, filed Nov. 15, 1999.

* cited by examiner

*Primary Examiner* — Kevin C Sirmons
*Assistant Examiner* — Bradley Osinski
(74) *Attorney, Agent, or Firm* — Fish & Richardson P.C.

(57) ABSTRACT

A skin attachment member having first and second surface with a plurality of skin penetrating elements extending integrally from the first surface of the backing to a distal tip. The skin penetrating elements are sized to avoid contact with nerves below the epidermal skin layer and have a foam disposed between at least some of the skin penetrating elements. A method of using the skin attachment member to deliver a pharmaceutical composition through the skin.

19 Claims, 10 Drawing Sheets

SKIN PENETRATING TOUCH FASTENERS

TECHNICAL FIELD

This application relates to skin penetrating touch fasteners.

BACKGROUND

Transdermal delivery of drugs (medications) has been around for a number of years. Transdermal delivery of drugs offers many advantages over more traditional routes of medicating a patient, i.e. oral administration of the medication or injection methods. One of the advantages of transdermal administration is that it avoids the negative side effects of oral administration, for example irritation of the gastrointestinal tract (some medicines cause ulcers and gastrointestinal bleeding). Transdermal administration also avoids hepatic and systemic toxicity that can result from the necessarily larger doses of the drag that have to be administered orally in order to compensate for hepatic first pass metabolism of drugs absorbed through the gastrointestinal tract, and to maintain therapeutic blood levels of the drug over the dosing interval. Moreover, transdermal delivery offers a painless, convenient, and non-invasive way to administer drugs, providing more stable blood levels with less frequent dosing because of controlled release of the medication. Unfortunately, without altering the skin's barrier these benefits can only be achieved for a few drugs that are able to cross the barrier established by the skin, such as some cardiac drugs and hormones.

The stratum corneum (composed of a lipid bilayers located between dead keratinocytes cells) provides the main resistance to drug delivery through the skin, limiting the transdermal route to drugs having a low molecular weight, i.e. less than 500 Daltons, and having the appropriate lipophilicity. Typically, drugs suitable for transdermal delivery are non-ionic, and/or have high potency, such that therapeutic effects can be achieved with small amounts of transdermal absorption. Other factors affecting absorption are the site of application, length of application, the addition of an absorption vehicle (penetration enhancer or enhancers), such as organic solvents like dimethyl sulfoxide (DMSO), and the integrity of the epidermal barrier. Transdermal delivery of drugs having a molecular weight of greater than 500 Daltons requires some type of skin permeation enhancement mechanism, such as chemical penetration enhancers. Therefore, transdermal administration of drugs has generally been limited to drugs having the required physiochemical properties allowing absorption through the epidermal layer.

Improvements in the transdermal delivery of drugs are sought, such as improvements that may lead to the applicability of transdermal delivery of drags to a broad group of medicines and higher molecular weight biomolecules.

SUMMARY

In one aspect the disclosure features a skin attachment member, which has a backing with a first surface and a second surface. A plurality of skin penetrating elements extend integrally from the first surface of the backing to a distal tip. The skin penetrating elements are sized to avoid contact with the nerves below the epidermal skin layer. The skin attachment member has a foam disposed on the first surface of the backing, such that at least a portion of the foam is disposed between at least some of the skin penetrating elements.

Some implementations may include one or more of the following features. The foam may be, for example, polyvinyl chloride (PVC) or polyurethane (PU). A pharmaceutical composition is disposed within the foam. The pharmaceutical composition may be in the form, for example, of a cream, a gel, or a liquid. In other implementations, the pharmaceutical composition is a biomolecule. The biomolecule can be a hormone or an antibody. In some implementations, the pharmaceutical composition is a small molecule. The pharmaceutical composition can be a controlled release formulation. The pharmaceutical composition can further include a vehicle. In some implementations, a penetration enhancer is disposed within the foam. An adhesive can be disposed on a surface of the foam. In some implementations, at least a portion of the foam extends to a height greater than the height of at least some of the skin penetration elements. In this and other implementations, a plurality of the skin penetrating elements may extend to a height greater than the foam.

In some implementations, a plurality of the skin penetrating elements have a groove extending lengthwise from the base towards the distal tip. e.g., from the base to the tip. Some of the skin penetrating elements have at least one retention barb extending from an outer side surface of the skin penetrating element. The base of the skin penetrating elements is a plastic resin. The skin penetrating elements have a height of about 0.004 to about 0.040 inches, for example, about 0.012 inches. In another aspect, the disclosure features a skin attachment member having a backing, which has a first surface and a second surface. A plurality of skin penetrating elements extend integrally from the first surface of the backing to a distal tip, and a foam is disposed on the first surface of the backing, such that at least a portion of the foam is disposed between at least some of the skin penetrating elements, the foam having a pharmaceutical composition disposed therein.

In another aspect, the disclosure features a method of delivering a pharmaceutical composition by attaching a skin attachment member to the skin of a subject, and maintaining the skin attachment member on the skin of the subject for a time sufficient to allow at least a portion of a pharmaceutical composition to permeate the epidermis of the subject. The skin attachment member has a backing, which has a first surface and a second surface, and a plurality of skin penetrating elements extending integrally from the first surface of the backing to a distal tip. The skin penetrating elements are sized to avoid contact with nerves below the epidermal skin layer. A plurality of the skin penetrating elements include at least one retention barb extending from an outer side surface of the skin penetrating element. A foam is disposed on the first surface of the backing, such that a portion of the foam is disposed between at least some of the skin penetrating elements. The pharmaceutical composition is disposed within the foam.

In some implementations, the method includes providing a skin penetrating enhancer. The skin penetrating enhancer is disposed within the foam. In other implementations, the method includes heating the skin attachment member. In some implementations, the method includes maintaining the skin attachment member on the subject for at least 2 hours, for at least 12 hours, for at least 24 hours, and for at least one week.

The details of one or more implementations are set forth in the accompanying drawings and the description below. Other features and advantages of the invention will be apparent from the description and drawings, and from the claims.

DETAILED DESCRIPTION

Figure 1:
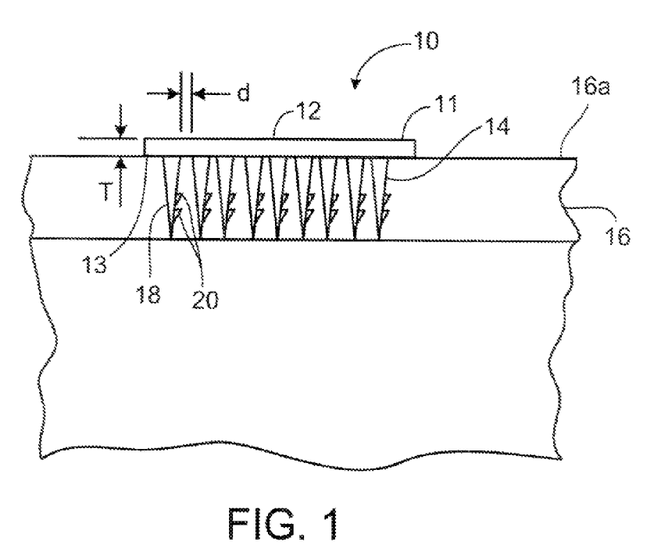
FIG. 1 is a highly magnified, side view of a section of a skin attachment member, shown secured in the epidermis.
Figure 2:
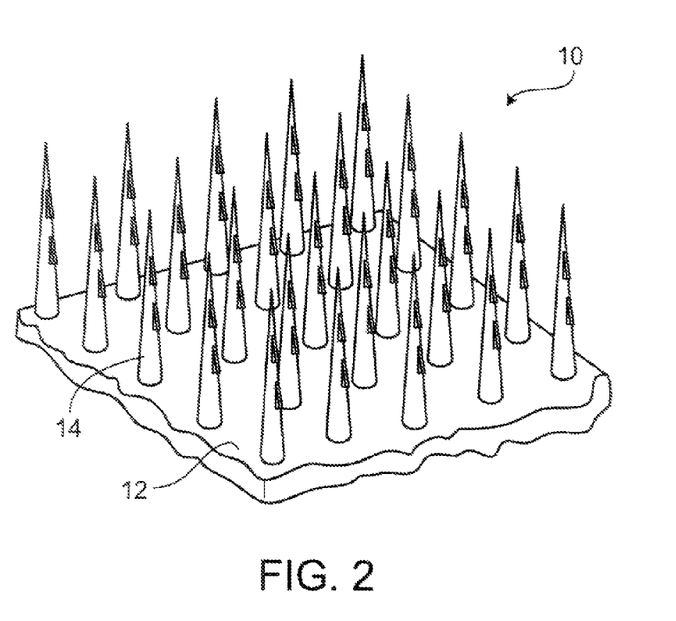
FIG. 2 is a diagrammatic perspective view of the section of the skin attachment member of FIG. 1.

Referring to FIGS. 1 and 2, a skin attachment member 10, formed of plastic resin, includes a backing 12 having an upper face 13 and a lower face 11, and multiple, parallel rows of integrally molded, pointed projections or elements 14 extending from backing 12 for penetrating into the epidermis 16. Although the pattern has been described as multiple, parallel rows of elements 14, different patterns of elements molded onto backing 12 can be used. The skin-penetrating elements 14 each, include a cone-shaped body 18 with one or more discrete barbs 20 extending from the body for securing skin attachment member 10 to epidermis 16.

The length of elements 14 is selected such that the elements do not penetrate so far into the skin as to contact nerves located below the outer layers of the epidermis causing significant pain and discomfort, but are long enough to cooperate with each other to provide sufficient adhesion to the skin. Elements 14 can be sized to extend into the portion of skin lying below the stratum corneum layer of the skin because of the small size of elements 14 and the spacing between nerves at this depth. For example, referring also to FIG. 3A, plastic elements 14 may have a length (height of the plastic elements 14), L, of about 0.10 mm (0.004") to 1.0 mm (0.04"), or preferably of about 0.20 mm (0.008") to 0.41 mm (0.016"), e.g., about 0.3 mm (0.012"). Since the thickness of the epidermis varies, for example, with age, the location on skin, and the gender of the patient, the length of elements 14 can be selected for the particular use.

Figure 3A:
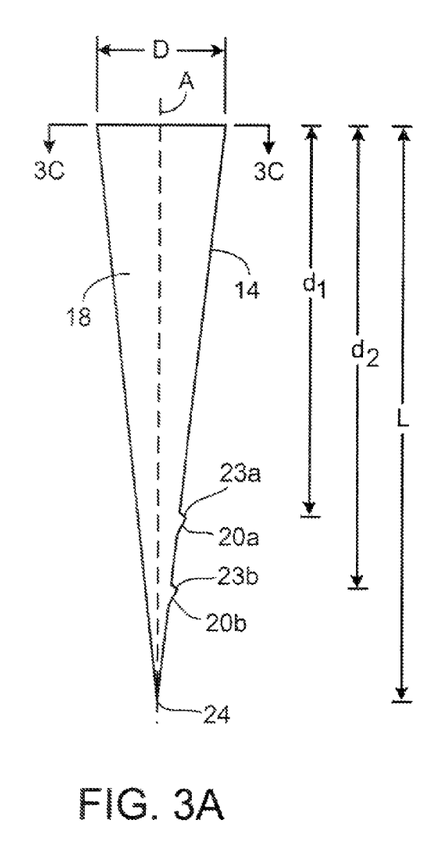
FIG. 3A is a side view of the skin-penetrating element of the skin attachment member of FIG. 1.
Figure 3B:
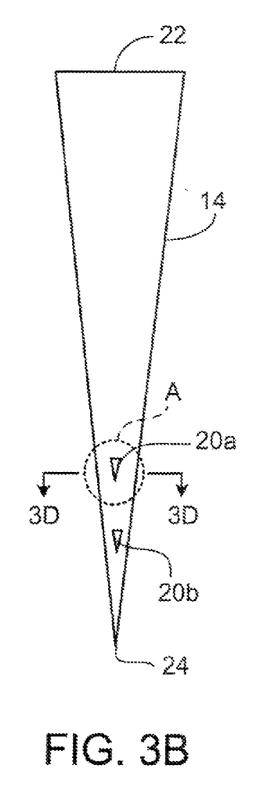
FIG. 3B is another side view of the element of FIG. 3A, rotated 90 degrees relative to FIG. 3A.

Referring, to FIGS. 3A and 3B, cone 18 tapers from a larger diameter proximal base 22 to a distal pointed tip 24. The tip may have an angle of about 10° to 35°, for example about 20°. The conical shape and sharp point of elements 14 ease their penetration into epidermis 16. The diameter of base 22 is selected to be large enough to help prevent breaking off of the projecting elements 14 from backing 12, while limiting the size of the opening made in the outer surface 16a of epidermis 16. For example, cone 18 may have a base diameter, D, of about 0.06 mm (0.002") to 0.4 mm (0.016"), e.g., about 0.1 mm (0.004"). Backing 12 may have a thickness, T, of about 0.08 mm to about 0.2 mm (0.003" to 0.008") to provide member 10 with sufficient handling characteristics.

The skin-penetrating projecting plastic elements 14 can be other than conical in shape. For example, elements 14 can be in the shape of a pyramid, a tetrahedron, or may be elliptical or square in cross-section, tapering to points at their distal ends. Rather than taper distally, elements 14 can progressively step down in diameter. Regardless of the particular shape selected, the elements 14 include sharp pointed tips 24 to ease tissue penetration.

Referring to FIGS. 3A and 38, projecting elements 14 are shown with two discrete barbs 20a, 20b for retaining the elements 14 in the skin, though fewer or more barbs can be disposed on cone 28 to provide the desired retention characteristics. The location of barbs 20 can be selected to take advantage of the greater elasticity of the skin portions lying below the stratum corneum to provide greater holding force. For example, barb 20a has a top surface 23a located a distance, $d_1$, of about 0.13 mm (0.005") to 0.25 mm (0.01"), for example about 0.2 mm (0.008") from base 22, and barb 20b has a top surface 23b located a distance, $d_2$, of about 0.18 mm (0.007") to 0.3 mm (0.012"), for example about 0.24 mm (0.0095") from base 22.

Figure 3D:
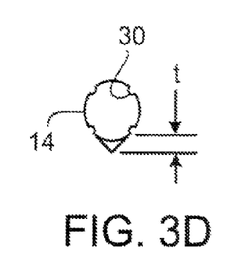
FIG. 3D is a cross-sectional view of the element of FIG. 3A taken along lines 3D-3D in FIG. 3B.
Figure 4:
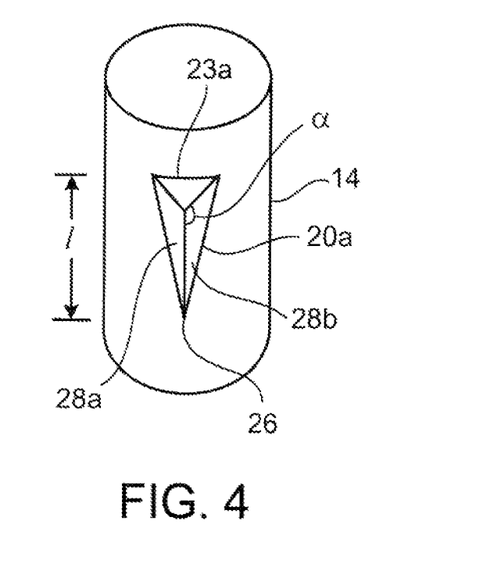
FIG. 4 is a perspective view of section A of FIG. 3B, showing a barb of the element of FIG. 3A.

Referring to FIG. 4, which is an enlarged view of section A of FIG. 3B, barbs 20a, 20b are roughly half-pyramids, each having a flat upper surface 23a which is perpendicular to a longitudinal axis, A, of the projecting element 14, and sloped sides 28a, 28b. Barbs 20a, 20b have a length, l, of about 0.0013 mm (0.00005") to 0.025 mm (0.001"), for example about 0.0025 mm (0.0001"), and a thickness, t (FIG. 3d), of about 0.0013 mm (0.00005") to 0.025 mm (0.001"), for example about 0.0025 mm (0.0001"), which tapers to a point 26 at an angle, α, of about 70° to 120°, for example about 90°.

Figure 5:
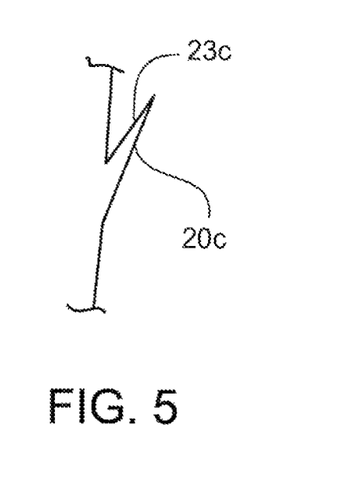
FIG. 5 shows an alternative embodiment of a barb.

In use, due to the elasticity of the skin, member 10 is secured to skin surface 16a by surrounding of the barbs by the epidermis. To improve retention of member 10 to the skin, the barbs can be angled as shown in FIG. 5. Here, a barb 20c has a sloped upper surface 23c.

The density of projecting elements 14 on backing 12 depends on use. For example, in high strain applications, a higher density provides better skin attachment, whereas, in applications in which member 10 is not subjected to high strain, a lower density is better for limiting the possibility of inflammation. If the density is too high, it can require too much force for elements 14 to penetrate into the skin. A density of about 10 to 40 projecting elements in 0.1 in$^2$ area, for example about 25 projecting elements in 0.1 in$^2$ area provides good skin attachment while not requiring excessive insertion force. In this case the projecting elements 14 are preferably spaced apart a distance, d (FIG. 1), of about 1 mm (0.040") to 2.5 mm (0.1"), for example about 1.6 mm (0.063").

Skin attachment member 10 and its projecting elements 14 are preferably formed from a thermoplastic, biocompatible polymer, which is stiff enough to penetrate skin but not brittle, and capable of filling a mold and retaining its molded form. Example of suitable polymers include nylon, polyethylene teraphthalate, and polyester. Also, bacteria killing agents, such as silver and/or copper and/or other bactericidal agents, or medication, such as an antibiotic, can be incorporated in the polymer from which member 10 is formed and/or a foam or gel 62 as shown in FIGS. 6A and 6B and discussed below.

Figure 3C:
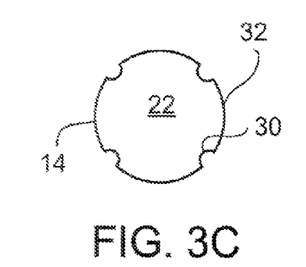
FIG. 3C is an end view of the element of FIG. 3A taken along lines 3C-3C in FIG. 3A.

FIGS. 3C and 3D show projecting elements 14 for use in drug delivery which include longitudinal grooves 30 in an outer surface 32 of cone 18. Although one or more grooves can be used, in this implementation four grooves 30 are shown, which provide passages for drug delivery as will be discussed in further detail below.

Figure 6A:
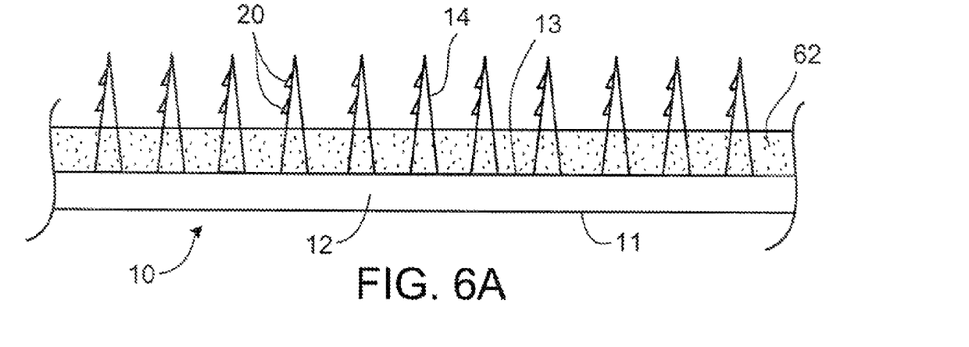
FIG. 6A is a side view of a skin attachment member with foam attached to the upper face of a sheet form base.
Figure 6B:
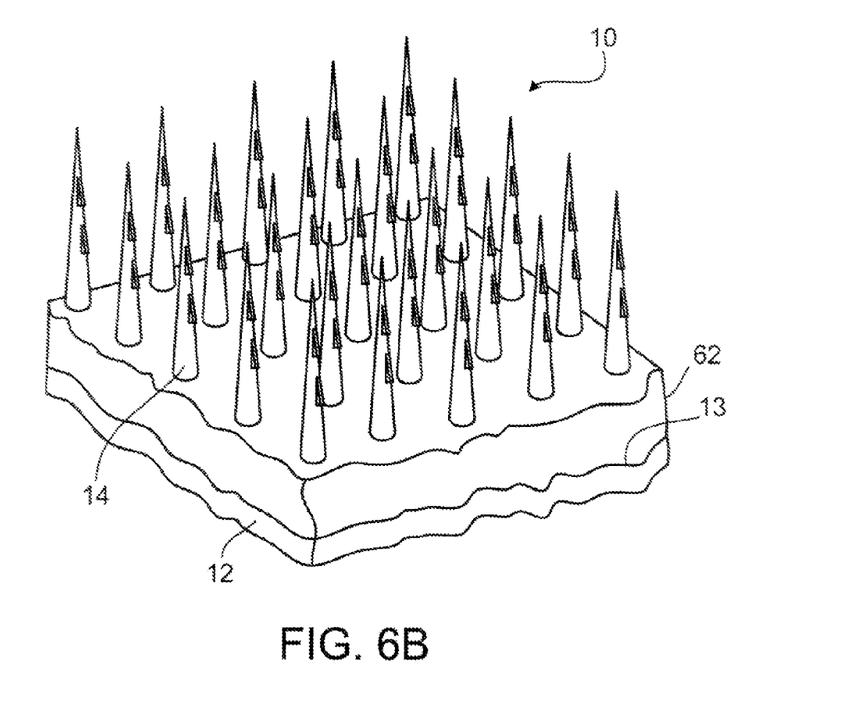
FIG. 6B is a perspective view of a skin attachment member of FIG. 2A.

Referring to FIGS. 6A and 6B, to facilitate transdermal delivery, skin attachment member 10 includes a foam or gel 62 in which the drug is placed, attached to upper lace 13. The foam or gel provides a reservoir for the drug allowing the drug to be released over time. The description that follows describes some implementations that include a foam, however in other implementations a gel can be used instead of the foam. The gel can be for example a soft-gel such as gelatin, sol-gel, aerogel, and hydrogel.

Referring again to FIG. 6A, the skin attachment member 10 includes the projecting elements 14 and the sheet form base 12 having an upper face 13 and a lower face 11. The projecting elements 14 extend from the upper face 13 of the sheet-form base 12, as discussed above. Attached (e.g., physically bonded) to the upper lace 13 of the sheet form base 12 is the foam 62. As depicted in FIG. 6B, the projecting elements 14 and foam 62 can cover substantially the entire upper face 13 of the sheet form base 12, allowing for varying sixes of skin attachment members.

Figure 7A:
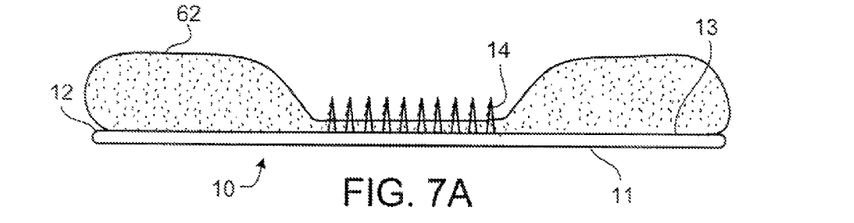
FIG. 7A is an end view of a skin attachment member having foam attached to the upper face of a sheet form base where foam extends longitudinally beyond an array of fastener elements on the upper face of the sheet form base.

In some implementations, e.g., as shown in FIG. 7A, the foam 62 substantially covers the upper face 13 of the sheet-form base 12, but the elements 14 do not substantially cover the upper face 13 of the sheet-form base 12. As shown in FIG. 7A, the foam can be of varying heights with the foam in areas that do not have elements 14 being higher than the foam that surrounds the elements 14.

Figure 7B:
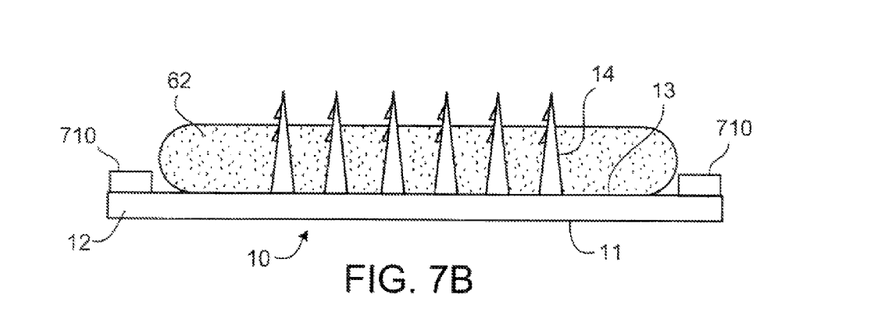
FIG. 7B is an end view of a skin attachment member having foam attached to the upper face of a sheet form base where foam extend longitudinally beyond an array of fastener elements on the tipper face of the sheet form base and having electrical elements on one or more peripheral edges.

In other implementations, the foam can have a substantially uniform height, e.g., as shown in FIG. 7B. In FIG. 7B, the foam 62 covers all of the upper face 13 of the sheet-form base 12 except for a perimeter area covered by an electrode 710, which can be used to supply an electric current that further enhances drug penetration, as will be discussed in further detail below.

Figure 8:
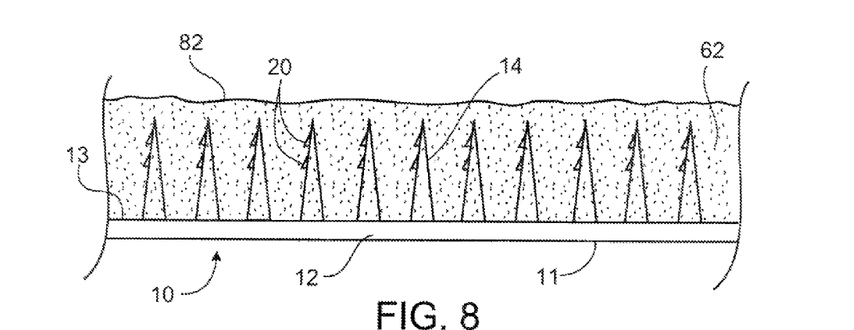
FIG. 8 is a cross-sectional view of a skin attachment member having foam attached to the upper face of a sheet form base, in which the height of the foam is greater than the height of the elements.

In some implementations, the foam springs hack to a thickness that is greater than the height of the fastener elements, causing the fastener elements to be entirely submerged in the foam when the foam is not compressed (see, e.g., FIG. 8).

FIG. 8 illustrates a skin attachment member 10 in which the height of the foam 62 is greater than the height of the elements 14. Although the projecting elements 14 are entirely submerged in the foam 62, the projecting elements 14 can push through the foam 62 and engage the epidermis 16, as discussed above. Thus, foam 62 also protects element 14 until skin attachment takes place, helping to prevent damage, breakage or contamination of the elements 14 during handling prior to use. In some implementations, a skin or film can be applied to the exposed surface of foam 62, or formed on the foam during the manufacture of the foam, forming a seal which can be punctured by elements 14 upon application to the skin, allowing a drug permeating the foam to pass through.

Figure 9:
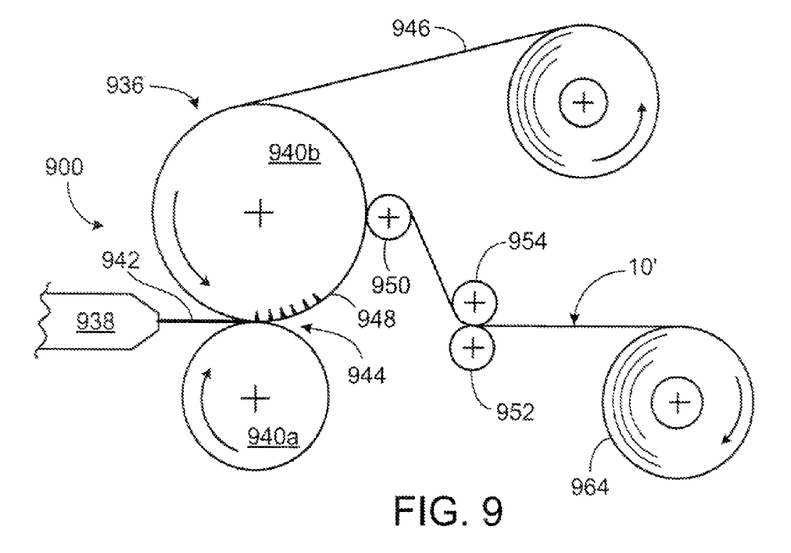
FIG. 9 shows schematically an apparatus and process for manufacturing a skin attachment member having foam attached to the upper face of a sheet form base.

FIG. 9 illustrates one method and apparatus for producing the above described skin attachment member. The method utilizes the continuous extrusion/roll-forming method for molding fastener elements on an integral, sheet-form base described in detail in U.S. Pat. No. 4,794,028, the disclosure of which is incorporated herein by reference. As shown in FIG. 9, skin attachment member 10 is formed by an extrusion apparatus 900 including a molding/calendaring assembly 936. The assembly includes an extrusion head 938, a base roll 940a, and a mold roll 940b. In FIG. 9, the relative position and size of the rolls and other components is not to scale.

The extrusion head 938 supplies a continuous sheet of molten resin 942 to a nip 944 formed between a base roll 940a and a mold roll 940b. As molten resin 942 enters nip 944, a sheet of foam 946 is fed through the nip 944 between the mold roll 940b and the molten resin 942. Due to pressure applied at the nip by rolls 940a and 940b, molten resin 942 is forced through the foam 946 into projecting-element forming cavities 948, forming the elements 14. A guide roller 950 is situated diagonally upwardly to assist in the removal of the finished touch fastener 100 from mold roll 940b. A set of upper and lower take-up rollers 952, 954 are situated forwardly of the guide roller 950. Downstream from the take-up rollers is a winder for winding continuous strip 10' on spool 964 for subsequent, shipment, storage and use.

Figure 10:
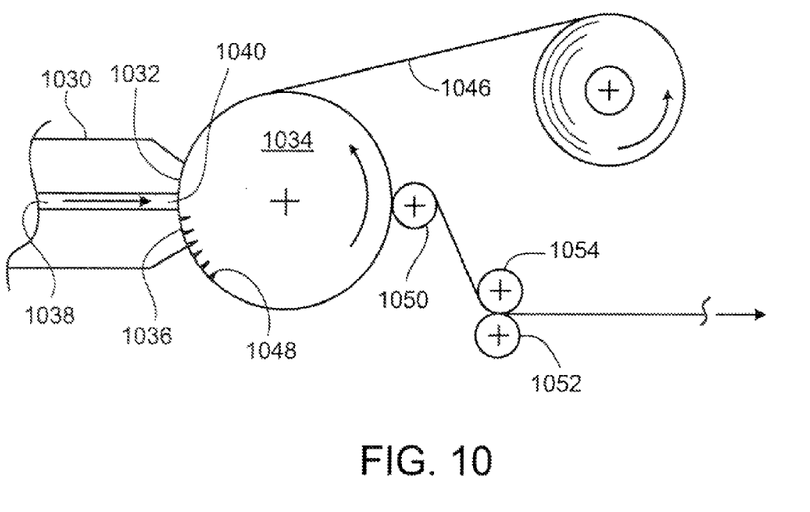
FIG. 10 shows schematically an apparatus and process for manufacturing a skin attachment member having foam attached to the upper face of a sheet form base.

FIG. 10 shows an alternative process for manufacturing a touch fastener having a foam embedded into the upper face of a sheet-form base. An injection die 1030 has an upper half arcuate surface 1032 that is substantially equal in curvature to a die wheel 1034, and a lower half surface 1036 having a curvature that defines a predetermined gap with respect to the curved surface of the die wheel 1034. The injection die 1030 has a resin extrusion outlet 1038, which is situated centrally of the upper and lower surfaces 1032, 1036 and from which molten resin 1040 is extruded in a sheet form under a predetermined pressure.

A sheet of foam 1046 is drawn from a roll and introduced between the upper arcuate surface 1032 of the injection die 1030 and the circumferential surface of the die wheel 1034. A guide roller 1050 is situated diagonally upwardly, and a set of upper and lower take-up rollers 1052, 1054 rotating at a speed slightly higher than the rotating speed of the die wheel 1034, are situated forwardly of the guide roller 1050.

The foam is compressed as it enters into the nip (as shown in FIG. 9) or the predetermined gap (as shown in FIG. 10), and is in a compressed state as the pressure forces the molten resin through the foam and into the hook cavities in the mold roll (FIG. 9) or the die wheel (FIG. 10). While foam generally springs back to its former thickness, a portion of the foam sticks (e.g., physically adheres or bonds) to the molten resin as it moves through the nip, and does not spring back to its original thickness. Thus, where the foam is embedded in the sheet form base, it generally has a thickness that is less than its thickness prior to adhering to the molten resin. Moreover, the portions of the foam in direct contact with the fastener elements also physically bond to the molten resin that enters into the mold cavity (948 or 1048), causing an even greater reduction in the springing back of the foam in areas of the sheet form base adjacent to fastener elements. The degree to which a foam springs back to it original thickness varies with the type and density of foam and is generally expressed as a percentage.

The structure of the mold roller 940*b* (die wheel 1034 has a similar structure) is substantially identical with the structure disclosed in U.S. Pat. No. 4,775,310, entitled APPARATUS FOR MAKING A SEPARATE FASTENER, which is incorporated herein by reference in its entirety. Mold roller 940*b* defines a multiplicity of projecting-element-forming cavities 948 with their bases opening to the circumferential surface of the die wheel. The mold roller 940*b* is driven to rotate in the direction indicated by the arrow in FIG. 9.

Figure 11A:
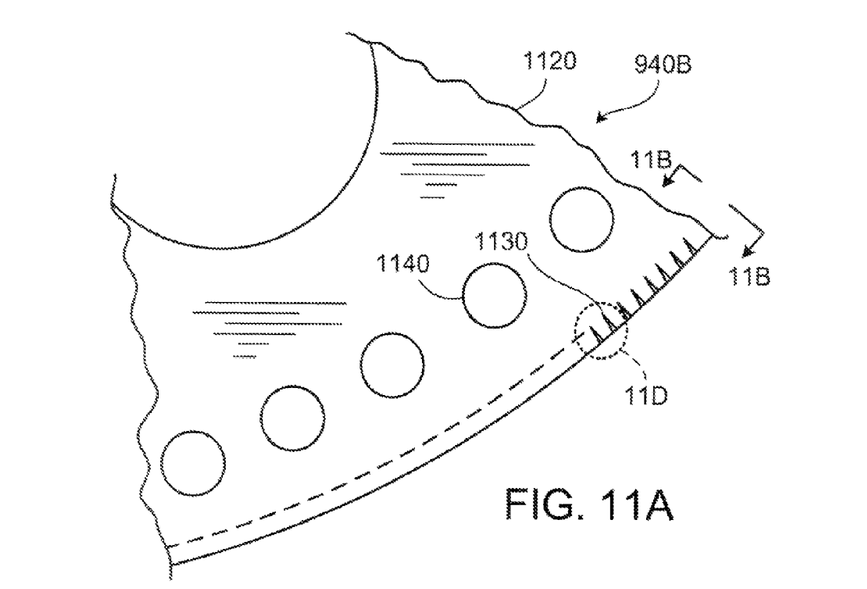
FIG. 11A is a side view of the mold roll of FIG. 9.
Figure 11B:
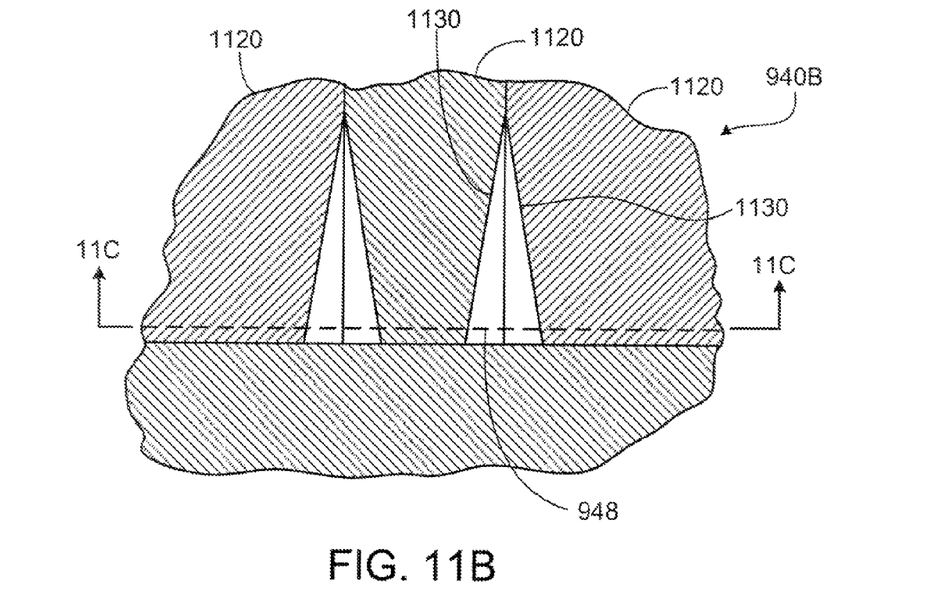
FIG. 11B is a cross-sectional view of a portion of the mold roll, taken along lines 11B-11B in FIG. 11A.

Roller 940*b* (die wheel 1034) is a cooled mold roll having a set of stacked parallel plates 1120 (FIG. 11B) in which edge formations 1130 define rows of projecting element-mold cavities 948. Roller 940*a* is a pressure roll which coacts with mold roll 940*b* for formation of continuous strip 10. Referring to FIGS. 11A and 11B, mold roll 940*b* includes a series of stacked plates 1120 having edge formations 1130 on either side of each plate. When stacked, plates 1120 together define projecting element-forming cavities 948 within which projecting elements 14 are formed. Plates 1120 also define water passages 1140 for cooling of continuous strip 10.

Figure 11C:
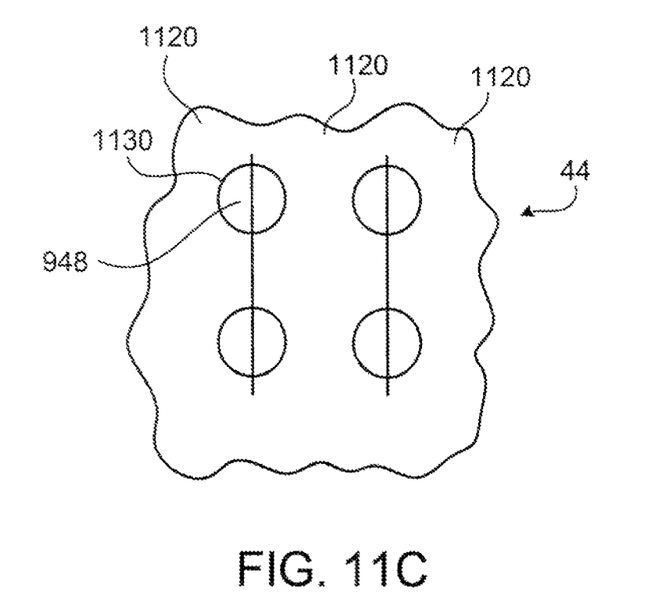
FIG. 11C is an end view of the mold roll, taken along lines 11C-11C in FIG. 11B.
Figure 11D:
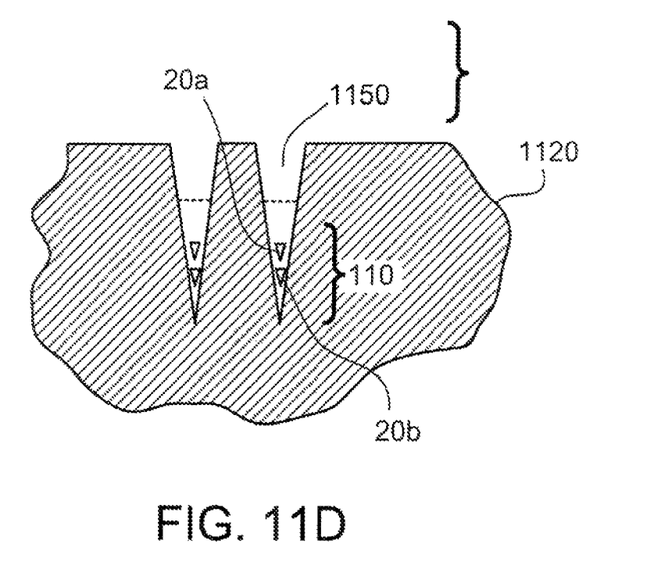
FIG. 11D is a magnified side view of portion 11D of the mold roll of FIG. 11A.
Figure 11E:
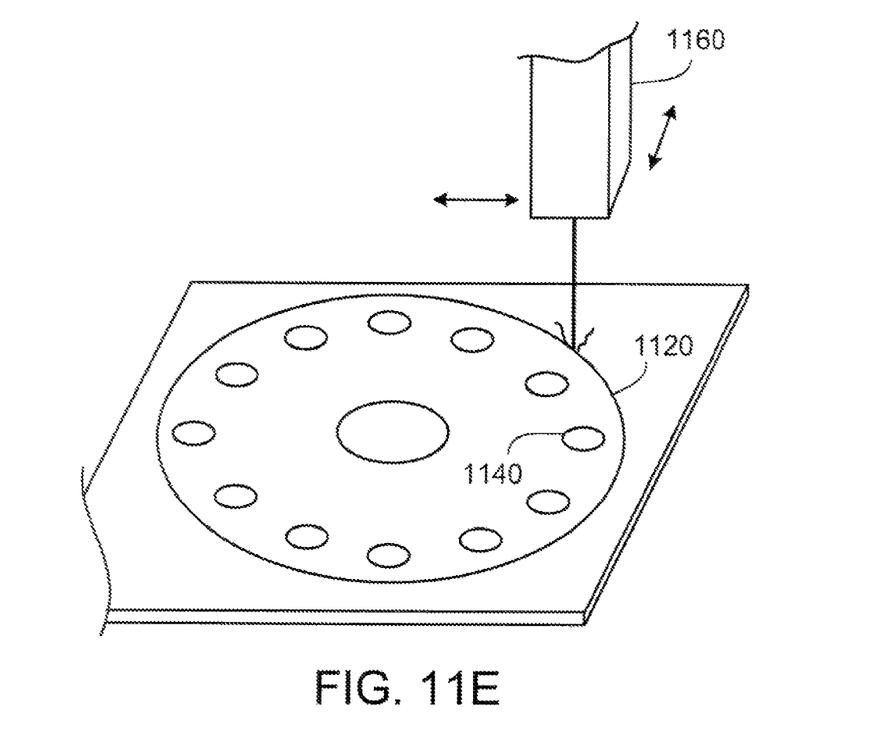
FIG. 11E shows laser machining of the mold roll.

Referring to FIGS. 11C and 11D, which is an enlarged view of sections 11C and 11D of FIGS. 11B and 11A respectively, plates 1120 of mold roll 940*b* can be formed by etching a cone shape 1150 for a length of about 0.004" from roll edge. The remaining tip portion 1110 of the cone is formed by laser machining (FIG. 11E) in which a laser 1160, under computer position control, is used to remove material from the plate to form the tip portion. Barb impressions 20*a*' and 20*b*' can also be formed using laser machining. The laser can also be controlled to form grooves 30 in cone 18 (shown in FIGS. 3A and C). The mold rolls are preferably formed of beryllium copper, the temperature of which is controlled during molding such that the resin does not cool too fast during application.

Figure 12:
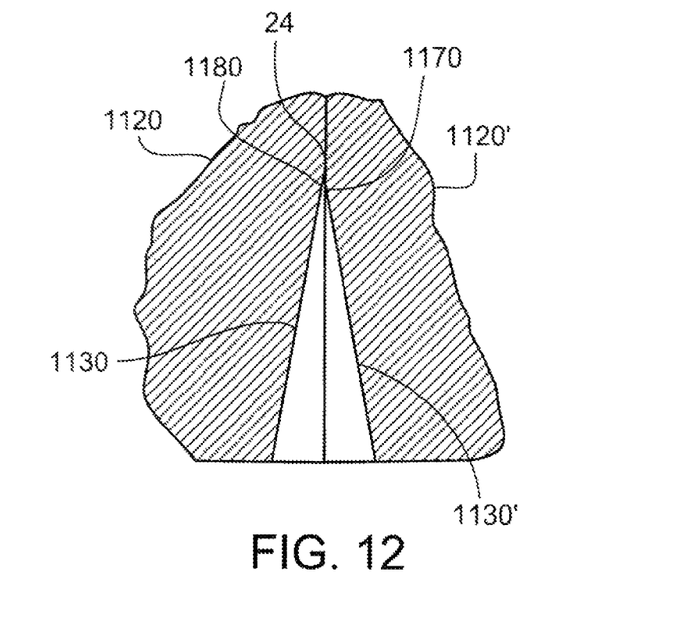
FIG. 12 shows art alternative edge formation on a mold roll.

FIG. 12 shows an alternative embodiment of a mold cavity in which a first plate 1120 defines an edge formation 1130 as described above, and a second plate 1120' defines an edge formation 1130' having a tip 1170 terminating prior to a tip 1180 of edge formation 1130. Thus, distal tip 24 of element 12 is defined by tip 1180. Suitable processes for making the skin attachment member and for attaching the skin attachment member to a foam are described in U.S. patent application Ser. No. 09/440,384, entitled SKIN ATTACHMENT MEMBER, the entire disclosure of which is hereby incorporated by reference, and further described in U.S. patent application Ser. No. 10/997,748, entitled MOLDED TOUCH FASTENERS AND METHODS OF MANUFACTURE, the entire disclosure of which is hereby incorporated by reference.

While skin attachment member 10 has been described as including multiple, parallel rows of projecting elements 14, the mold rolls can be arranged such that the rows of elements 14 are offset or otherwise distributed on backing 12. The elements 14 can be arranged such that they are completely or partially covered by foam 62. Additionally, the elements 14 can be formed in groups such that there are areas of foam on skin attachment member 10 with and without the projecting elements 14. The foam without projecting elements 14 can surround an area having both projecting elements 14 and foam. The projecting elements 14 can also be formed such that their longitudinal axes are not perpendicular to backing 12 or are distributed at various angles to hacking 12. While enough of the projecting elements 14 should include barbs 20 to provide the desired degree of securement to the skin, not all of projecting elements 14 need include barbs 20.

The foam 62 of the skin attachment member is made from a material that is permeable to a selected drug and allows the drug to be delivered at a controlled rate. The foam material can be made from biocompatible polymers, copolymers, silicone rubbers, or any other material having the correct properties to allow for controlled drug delivery. The selection of the foam material will depend upon the physical properties of the foam material and their interaction with the particular drug to be administered. Examples of materials that can be used are polyolefin, polyvinyl chloride, poly (ethylene), poly (vinyl alcohol), poly (urethanes), poly (siloxanes), acrylic, polyisobutylene, polydimethylsiloxane, and polyether The skin attachment members 10 described above can be made in a continuous sheet form and cut into any shape. For example, the skin attachment members 10 can be die-cut. Suitable processes for cutting a skin attachment member into a shape by die cutting are described, e.g., in U.S. Pat. No. 5,286,431, to Banfield et al., entitled MOLDED PRODUCT HAVING INSERT MOLD-IN FASTENER, the entire disclosure of which is herein incorporated by reference, and are further described in U.S. Pat. No. 5,766,385, to Pollard et al., entitled SEPARABLE FASTENER HAVING DIE-CUT PROTECTIVE COVER WITH PULL TAB AND METHOD OF MAKING SAME, the entire disclosure of which is incorporated herein by reference.

Alter making and cutting the skin attachment member to the desired shape, a drug or a drug and a penetration enhancer is applied to the foam before application to a person's skin. Suitable penetration enhancers are discussed below. Depending on the consistency of the drug (or drug/enhancer combination), the drug can be sprayed onto the loam (for a liquid), spread over the foam (for a paste, cream, or a gel), or soaked into the foam (for a liquid, cream, or a gel). Typically, transdermal administration of drugs has been limited to drugs having a molecular weight of less than about 500 Daltons and having the proper degree of lipophilicity, and having a melting point of less than 200° C. However, through the use of projecting elements 14, which create a passage through the epidermal layer, larger molecular weight molecules can be administered transdermally. The following are some (but not all) examples of the drugs that can be administered transdermally using the skin attachment member described herein: nitroglycerin, scopolamine, nicotine, clonidine, and fentanyl, estradiol, tulobuterol, testosterone, alprostadil, buprenorphine, dexamethasone, dextroamphetamine, androgen/estradiol, estradiol/progestin, testosterone/estradiol, flurbiprofen, lidocaine, albuterol, enalapril, dronabinol, ketorolac, alprazolam, cytarabine, atenolol, buprenorphine, isosorbide dinitrate, and prazosin also larger molecular weight molecules like glucagon-like peptide-1, parathyroid hormone, insulin, calcitonin, vaccines, RNAi, antibodies, and other biomolecules and macromolecules can be delivered transdermally.

Figure 13A:
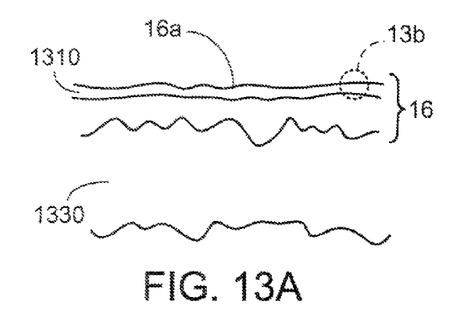
FIG. 13A shows the different layers of a segment of skin.
Figure 13B:
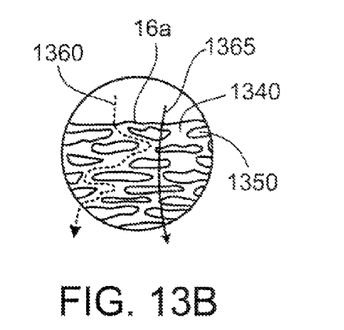
FIG. 13B is a enlarged view of the section 13B shown in FIG. 13A.

In order to deliver drugs transdermally, the drugs must pass through the skin's natural barriers. Referring to FIG. 13A, the skin consists of two main layers: the epidermis 16 and the dermis 1330. These layers contain, among other things, blood vessels that allow the drugs to be absorbed into the circulation and nerves. The main barrier to permeability of a drug is a layer of the epidermis called the stratum corneum 1310. The stratum corneum, seen greatly magnified in 13B, is composed of several layers of flattened, dead keratinocytes (horny cells)

1350 connected by desmosomes and embedded in a lipid matrix 1340 forming a "brick and mortar" type of barrier to drug penetration. Typically, drugs pass through the stratum corneum's "brick and mortar" barrier by two main routes consisting of the transcellular route 1365, where the drugs have to pass through multiple layers of dead keratinocytes and lipid, and the intercellular route 1360, where drugs pass through the lipid layers between the cells. Because of this "brick and mortar" type barrier the skin is relatively impermeable to molecules having a molecular weight of greater than 500 Daltons, and to molecules which do not have the proper solubility in both water and lipid unless a process other than permeability of the drug is used to breach this barrier.

Figure 13C:
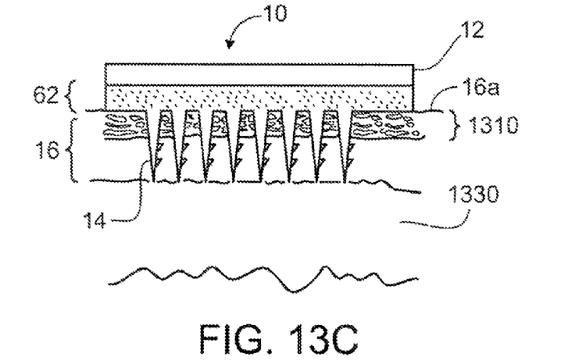
FIG. 13C shows a highly magnified view of the skin attachment member with foam attached secured to the epidermis.

In order to breach this barrier and make drugs more permeable through the skin, a person can apply skin attachment member 10, having the desired drug permeated into the foam, to the outer surface of the skin 16a causing elements 14 to penetrate into the epidermis. FIG. 13C shows the skin attachment member 10 with elements 14 penetrating into the epidermis 16 and foam 62 containing the desired drug in contact with the outer surface of the epidermis 16a. Elements 14, having grooves 30 (FIG. 3C), form passages through the "brick and mortar" barrier of the stratum corneum by penetrating through the stratum corneum. Thus, the passages created by the elements 14 allow both smaller and larger molecular weight molecules to pass through the barrier increasing the rate of absorption for both, while at the same time not causing pain because they do not penetrate into the dermis 1330 where the nerves are located.

Skin penetration can be further enhanced by combining a chemical penetration enhancer with the drug. Chemical enhancers improve the transport of the drug across the "brick and mortar" barrier of the epidermal layer. A variety of enhancers exist, and they work by altering the structure of the skin lipids and/or enhancing the solubility of the diffusing drug. Some enhancers extract lipids from the stratum corneum, some disrupt the lipid matrix structure, some displace bound water, some loosen horny cells, some alter the skin partitioning coefficient, and some delaminate the stratum corneum. Examples of penetration enhancers are alcohols (such as methanol and ethanol), DMSO, and DMF. DMSO, in concentrations as low as 2 percent, will improve topical absorption of drugs without creating the taste and smell associated with higher concentrations of the chemical. By adding the penetration enhancer to the drug incorporated into foam 62 of skin attachment member 10, the drug's permeability through the stratum corneum 1310 is increased.

The time period for which skin attachment member 10 is applied to the skin, allowing the drug to permeate out of the foam and through the skin, is determined by the physical properties of the drug and the foam. Depending on the respective physical properties, the skin attachment member 10 may stay attached from a period of several minutes to several days. Typical examples of the time period that the drug can be applied to the skin include 30 minutes, 1 hour, 2 hours, 4 hours, 6 hours, 12 hours, 24 hours, 2 days, etc. As long as there is drug available in the foam for delivery through the skin at a rate appropriate to achieve the desired clinical response, the skin attachment member may remain attached to the skin. The duration for which the skin attachment member is applied can be extended by incorporating a timed release formulation of the drug into the foam or by using foam with the appropriate timed release characteristics. This allows the drug to be delivered over an extended, time period with less frequent need to replace the skin attachment member as the drug is depleted. Other methods for timed release of the drug include microencapsulation.

Figure 13D:
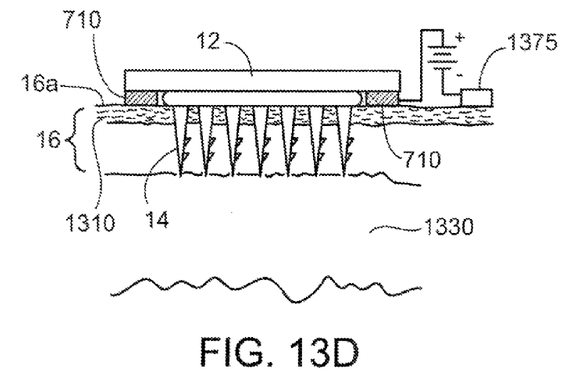
FIG. 13D shows a highly magnified view of the skin attachment member and attached foam with a strip of conductive material attached to a non-foam covered peripheral edge of the upper face.

In some implementations, drug delivery is controlled by using an electric current to drive the drug through the skin barrier. This process can be continuous or can be intermittent (or continuous with an intermittent bolus) on a predetermined time schedule and/or controlled by a sensor which determines when the drug needs to be given. FIG. 13D shows the skin attachment member 10 of FIG. 8 attached to the surface of the epidermis 16a, so that electrode 710 contacts the skin. A voltage V1 is applied between electrode 710 and electrode 1375 positioned on another area of the skin surface. For a positively charged drug molecule 1380 (or drug molecule mixed with penetration enhancer), electrode 710 acts as an anode and causes the positively charge molecule 1380 to flow away from the electrode and out of the foam through the skin barrier into the dermis where the drug can be absorbed into the circulation. For negatively charged molecules, the voltage is reversed causing the negatively charged molecules to migrate away from the electrode 710 through the skin barrier. In some implementations, a sensor (not shown) monitors a parameter, such as blood glucose level, and activates the circuit applying the appropriate voltage to electrode 710 when the parameter dictates that the drug needs to be delivered. In this manner, there can be a continuous delivery of drug at a lower rate of permeability, and then an enhanced delivery of the drug when the sensor activates the electrode. Thus, the permeation of the drug through the skin can be modified by the combination of skin penetration elements 14, and/or the penetration enhancer, and/or the electric current applied by means of the electrode 710.

Similarly, a resistive element (not shown), capable of producing heat in response to a current, can be applied to the skin attachment member 10 (instead of electrode 710), and a current can be generated through the resistive element by applying voltage V1 across the resistive element. In this manner, the resistive element produces a local heating effect causing the drug to permeate through the skin more readily. The resistive element can be applied either peripherally around the foam as is shown for the electrode 710, or to the lower face 11 (or in any other location on skin attachment member 10 that produces a local heating effect), allowing the heat to pass through the skin attachment member 10 and heat the drug, foam and skin underneath, causing increased skin permeability.

A number of implementations of the invention have been described. Nevertheless, it will be understood that various modifications may be made without departing from the spirit and scope of the invention.

For example, different patterns of elements 14 can be formed on sheet form base 12, as well as different heights and/or distribution of foam 62 on sheet form base 12. The distribution and relationship of the foam 62 to the elements 14 can vary depending on the application. The elements can be sized and/or shaped differently as discussed above, and/or have a different number and/or shape of the barbs 20. Different types of foam can be attached to the sheet form base and different types of medications can be used for application by the skin attachment member 10, as well as different types of penetration enhancers.

In an alternate method of making the skin attachment member 10 with the foam attached, a sheet form base 12, having an upper face 13 and a lower face 11 and elements 14 positioned on the upper face 13, is positioned on a base roll. A foam material 62 having openings (e.g., slits or holes) is positioned on a material roll. Pressure is applied to the sheet form base and foam material at the nip of the base roll and material roll while the sheet form base 12 and the foam material 62 are pulled simultaneously from the base roll and material roll. The pressure causes the male fastener elements 14 of the sheet form base 12 to engage the foam material 62 in the portions of the foam having holes.

Accordingly, other embodiments are within the scope of the following claims.

What is claimed is:

1. A skin attachment member comprising;
 a backing having a first surface and a second surface;
 a plurality of skin penetrating elements extending integrally from the first surface of the backing to a distal tip, the skin penetrating elements being sized to avoid contact with nerves below the epidermal skin layer; and
 a foam disposed on the first surface of the backing, wherein at least a portion of the foam is disposed between at least some of the skin penetrating elements, wherein at least some of the skin penetrating elements each include a retention barb extending from an outer side surface of the skin penetrating element;
 wherein at least a portion of the foam extends to a height greater than the height of at least some of the skin penetrating elements.

2. The member of claim 1 wherein a pharmaceutical composition is disposed within the foam.

3. The member of claim 2 wherein the pharmaceutical composition is in the formulation of a cream, a gel, or a liquid.

4. The member of claim 2 wherein the pharmaceutical composition comprises a biomolecule.

5. The member of claim 4 wherein the biomolecule is selected from the group consisting of a hormone or an antibody.

6. The member of claim 2 wherein the pharmaceutical composition comprises a molecule having a molecular weight greater than 500 Daltons.

7. The member of claim 2 wherein the pharmaceutical composition comprises a controlled release formulation.

8. The member of claim 2 wherein the pharmaceutical composition further comprises a vehicle.

9. The member of claim 1 wherein a plurality of the skin penetrating elements comprise a groove extending lengthwise from the base to the distal tip.

10. The member of claim 1 wherein the base comprises a plastic resin.

11. The member of claim 1 wherein the skin penetrating elements have a height of about 0.004 to about 0.040 inches.

12. The member of claim 1 wherein the skin penetrating elements have a height of about 0.012 inches.

13. The member of claim 1 wherein an adhesive is disposed on a surface of the foam.

14. The member of claim 2 wherein a skin penetration enhancer is disposed within the foam.

15. The member of claim 1 wherein the foam comprises PVC.

16. The member of claim 1 wherein the foam comprises PU.

17. The member of claim 1, wherein the backing incorporates a bacterial killing agent.

18. The member of claim 17, wherein the bacterial killing agent is silver.

19. The member of claim 1, wherein a protective film covers at least part of an exterior surface of the foam.

* * * * *

UNITED STATES PATENT AND TRADEMARK OFFICE
CERTIFICATE OF CORRECTION

PATENT NO. : 8,439,861 B2
APPLICATION NO. : 11/739244
DATED : May 14, 2013
INVENTOR(S) : Howard A. Kingsford Page 1 of 1

It is certified that error appears in the above-identified patent and that said Letters Patent is hereby corrected as shown below:

In the Claims:

Claim 14, col. 12, line 19, delete "claim 2" and insert --claim 1--.

Signed and Sealed this
Sixth Day of August, 2013

Teresa Stanek Rea
*Acting Director of the United States Patent and Trademark Office*